United States Patent [19]
Topp et al.

[11] 3,978,006
[45] Aug. 31, 1976

[54] METHODS FOR PRODUCING OXYGEN-SENSING ELEMENT, PARTICULARLY FOR USE WITH INTERNAL COMBUSTION ENGINE EXHAUST EMISSION ANALYSIS

[75] Inventors: Bernhard Topp, Gerlingen; Horst Neidhard, Korntal; Rudolf Pollner, Kornwestheim; Karl-Hermann Friese, Leonberg, all of Germany

[73] Assignee: Robert Bosch G.m.b.H., Gerlingen-Schillerhohe, Germany

[22] Filed: Sept. 23, 1974

[21] Appl. No.: 508,250

Related U.S. Application Data

[62] Division of Ser. No. 259,134, June 2, 1972, abandoned.

[30] Foreign Application Priority Data
Feb. 10, 1972  Germany.............................. 2206216

[52] U.S. Cl........................... 252/477 R; 204/195 S; 60/276
[51] Int. Cl.².................... B01J 35/00; F01N 3/00
[58] Field of Search............. 252/477 R; 204/195 S; 23/288 FC; 123/22; 60/276

[56] References Cited
UNITED STATES PATENTS

| | | | |
|---|---|---|---|
| 2,965,583 | 12/1960 | Houdry et al................... | 252/477 R |
| 3,347,767 | 10/1967 | Hickam.............................. | 204/195 |
| 3,468,780 | 9/1969 | Fischer .............................. | 204/195 |
| 3,645,875 | 2/1972 | Record et al....................... | 204/195 |
| 3,844,920 | 10/1974 | Burgett et al..................... | 204/195 S |
| 3,906,721 | 9/1975 | Micheli et al........................ | 60/276 |

*Primary Examiner*—Carl F. Dees
*Attorney, Agent, or Firm*—Flynn & Frishauf

[57] ABSTRACT

Methods for making an exhaust-gas-sensing element which is an oxygen concentration cell having a solid electrolyte with an electron-conductive surface on the side exposed to the reference air and a catalytic electron-conductive layer containing micro pores which extend through to the solid electrolyte on the other surface which is adapted to be exposed to the exhaust gases. The electron-conductive catalytic layer is covered with a porous protective layer. The method comprising applying the catalytic layer by means of thin layer techniques and then heating to form the micro pores; or by applying a paste comprising ceramic particles, catalytic particles and a thinning oil and sintering.

15 Claims, 5 Drawing Figures

METHODS FOR PRODUCING OXYGEN-SENSING ELEMENT, PARTICULARLY FOR USE WITH INTERNAL COMBUSTION ENGINE EXHAUST EMISSION ANALYSIS

This is a division of application Ser. No. 259,134, filed June 2, 1972 now abandoned.

CROSS REFERENCE TO RELATED PATENT AND APPLICATIONS

U.S. Pat. No. 3,483,851, Reichardt, Dec. 16, 1969.
U.S. Ser. No. 239,740, filed Mar. 30, 1972, Zechnall et al., now U.S. Pat. No. 3,745,768.
U.S. Ser. No. 259,157, filed June 2, 1972, Schmidt et al.
U.S. Pat. No. 3,759,232, Wahl et al., Sept. 18, 1973.
U.S. Pat. No. 3,782,347, Schmidt et al., Jan. 7, 1974.
U.S. Ser. No. 298,108, filed Oct. 16, 1972, Wahl et al.

The present invention relates to a sensing element for electro-chemical sensing of oxygen content in gases, and particularly in the exhaust gases of internal combustion engines, and to a method of making such a sensing element. The oxygen sensed by the element is sensed by sensing oxygen concentration with an ionically conductive solid electrolyte, the outer surface of which is covered with an electron conductive layer.

Internal combustion engines, and particularly automotive internal combustion engines have exhaust gases which contain carbon monoxide, nitrogen oxides, and non-oxidized, that is unburned or only partially burned hydrocarbons. All these substances contribute to air pollution. In order to reduce these substances which cause air pollution to a minimum value, it is necessary to clean the exhaust gases from the internal combustion engines as much as possible by effectively removing the largest possible quantity of the substances from the exhaust gases. This means that carbon monoxide and unburned hydrocarbons should be oxidized as completely as possible into their next higher oxidation stage, namely carbon dioxide and water (for the hydrocarbons), and the nitrogen-oxide compounds should be converted to elemental nitrogen and oxygen.

Conversion of the noxious components of exhaust gases to non-poisonous compounds like carbon dioxide, nitrogen and water, can be obtained by subjecting the exhaust gases to after-burning, that is, by subjecting them to temperatures above about 600° C while exposed to catalysts. In order to succeed in this method, however, the composition of the exhaust gases must be so controlled that practically complete conversion of the exhaust gases to the non-poisonous compounds is possible. This means that the relationship of air to fuel is close to the stoichiometric value. As a measure of the stoichiometric value, the air number $\lambda$ has been used. At a value of $\lambda = 1$, the relationship of air to fuel is stoichiometric. If no excess oxygen is present which exceeds the equilibrium of the various possible reactions, $\lambda \leq 1$. If, however, $\lambda \geq 1$, excess oxygen is present in the mixture. At $\lambda = 1$, the gas changes from a reducing to an oxidizing state.

The value of the air number $\lambda$ at approximately one requires that a sensing element be provided which is exposed to the exhaust gases and which determines oxygen content; this sensing element is then connected over a control device to the fuel or air supply, or to both, to provide the correct ratio of fuel and air components of the mixture applied to the internal combustion engine, so that the exhaust gases will have as low a value of noxious components as possible.

Sensing elements which operate on the principle of elemental oxygen concentration and utilizing ion conductive solid electrolytes have been proposed — see German Publication Paper DT-OS No. 2,010,793. This publication illustrates a sensor which is mounted fixedly in the wall of an exhaust duct and which utilizes ambient air as a reference system to determine the elemental oxygen concentration; the solid electrolyte, at both sides, is covered at least in part with platinum. It has been found that such a sensing element does not deliver a sharp voltage variation at the point $\lambda = 1$. Rather, the voltage changes over a wider range of $\lambda$ in a gradual, continuous manner. Sensors should, however, preferably provide outputs which can be applied to a control system in which the change in voltage value at $\lambda = 1$ is very sharp.

It is an object of the present invention to provide an electro-chemical sensing element to determine the oxygen content in gases, and more particularly in exhaust gases of internal combustion engines, especially for automotive use, and which deliver a sharply varying voltage signal at an air number of $\lambda = 1$, which have rapid response time, and are reliable in operation for long periods of time.

A sharp change in output voltage can only be obtained when the components of the exhaust gases are in thermo-dynamic equilibrium. This, normally, is not the case however.

SUBJECT MATTER OF THE PRESENT INVENTION

Briefly, a solid electrolyte stratum, or body is provided which is exposed at one side to the gases, the oxygen content of which is to be indicated. An electron conductive layer is placed on this side of the solid electrolyte body, the electron conductive layer being protected from mechanical and chemical damage. This electron conductive layer catalyzes the equilibrium condition of the gas and, at least at those points at which its thickness is greater than 100 to 300 A (1,000 to 3,000 nm, that is, milli-microns, or nanometers), is formed with micro pores or micro fissures which extend through the layer to the surface of the solid electrolyte. The fissures or pores have a diameter, or a width which is less than about half of the average thickness of the layer; the solid electrolyte itself is not exposed to the gases directly. Oxygen concentration cells can, in principle, determine the residual oxygen content as well as the oxygen content which is thermodynamically in equilibrium, and which is present in the gases.

The invention will be described by way of example with reference to the accompanying drawings, wherein.

Figure 1:
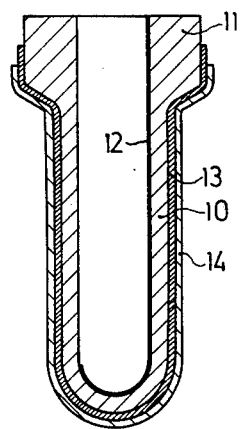
FIG. 1 is a cross-sectional, schematic view through one form of the sensing element.
Figure 2:
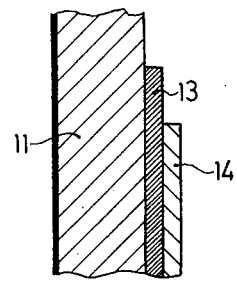
FIG. 2 is an enlarged fragmentary view of one side of the sensing element.

The sensing element of FIG. 1 has an outer surface which is completely covered with a platinum layer. The sensor body is a solid electrolyte in form of a tube 10, closed at one end. The open end is formed with a boss or ring 11. The interior of the tube has an inner electrode 12, in the form of a conductive path of noble metal, or of an electron conductive material (at operating temperature) such as a simple or composite oxide. The outer surface of the solid electrolyte tube 10 is completely coated with a platinum layer 13, which extends up to the boss 11. The platinum layer, in turn, is covered with a porous protective layer 14, so that only a small portion of the platinum layer, adjacent the boss 11 is free from the covering, to permit connection of a terminal or electrode wire. FIG. 2 illustrates a fragmentary, enlarged cross section through a portion of the boss 11 at that point at which the platinum layer and the porous protective layer 14 terminate. As seen, the platinum layer 13 is not completely covered to the end by the porous protective layer 14 to provide for an electrical contact to platinum layer 13.

Figure 3:
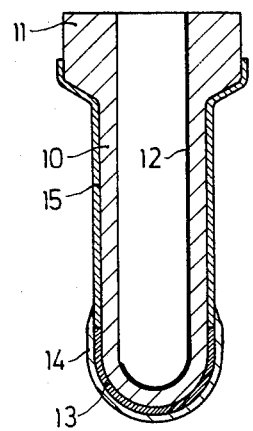
FIG. 3 is a schematic longitudinal cross-sectional view of another embodiment of a sensing element.
Figure 4:
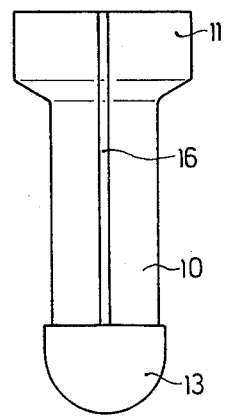
FIG. 4 is a front view of the sensing element in FIG. 3.
Figure 5:
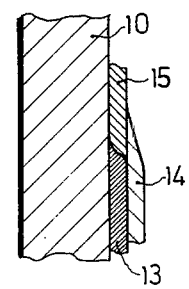
FIG. 5 is a fragmentary enlarged view of a wall portion of the sensing element of FIGS. 3 and 4.

FIG. 3 illustrates an embodiment in which only the head portion of the solid electrolyte tube is covered with a platinum layer 13. The remaining portion of the outer surface is covered with a gas-tight layer 15, so that no exhaust gases can directly impinge on the solid electrolyte body 10. The platinum layer again is covered by a porous protective layer 14. The platinum layer is contacted — as seen in FIG. 4 — by a small conductive path 16 extending from the platinum layer 13 to the boss 11. The inner electrode 12 is similar to that of the embodiment of FIG. 1. FIG. 5 illustrates the platinum layer 13 and the gas-tight layer 15 being overlapped by the porous protective layer 14, in order to provide for good protection of the platinum layer 13.

The remaining, or excess oxygen in the exhaust gases of internal combustion engines, or the unreacted oxygen in the exhaust gases, upon insufficient oxidation, is indicated by the oxygen concentration, if the solid electrolyte is coated with catalytically inactive metals, or with inactive electronically conductive oxides, respectively, The concentration of oxygen indicates the transition of lean ($\lambda > 1$) to rich ($\lambda < 1$) mixture by a roughly constant change in voltage which, however, is not clearly defined at the point of $\lambda = 1$, since the remaining oxygen content will not have a clearly defined relationship with the temperature and the air-fuel mixture. The remaining or excess oxygen within the exhaust gases, which is measured by the oxygen concentration, depends on the type of motor, temperature, flow of gas at the solid electrolyte, and on other parameters.

The voltage difference, as the value of $\lambda$ changes from less to greater than 1 can be determined reproducibly if the oxygen content within the exhaust gases, which is thermo-dynamically in balance, is sensed. The output potential E depends, based on the Nernst equation, only on temperature and that oxygen content which is in balance, within the exhaust gases. As a characteristic, at $\lambda = 1$, that is, upon transition from reducing to oxidizing atmosphere, a voltage jump of several 100 mV will be sensed. The position of the voltage jump at $\lambda = 1$ is independent of temperature. The value, or amplitude depends on temperature and varies somewhat between 300 to 400 mV.

The oxygen content which is thermo-dynamically in balance can be sensed when the exhaust gases, which are at a temperature in excess of 450° C, contact a securely adhering catalyzing layer, applied to the solid electrolyte surface, and exposed to the exhaust gases. This catalyzing layer determines or sets the gas equilibrium. This layer should not have large pores or surfaces directly exposed to the exhaust gases, since otherwise excess or remaining oxygen molecules can reach the solid electrolyte surface directly, and then voltages depending on mixtures are measured. This leads to the previously experienced result that the voltage does not change rapidly, in jumps, almost in a binary manner, but rather is continuously variable, as above described in connection with measuring of remaining or excess oxygen.

To provide effective control of emission or exhaust gases, low response time is required. A response time of from 1 to 100 msec (milli-second or $10^{-3}$ second) — depending on temperature at the surface of the solid electrolyte — can be obtained when the catalyzing layer is formed with micro pores or micro fissures which permit gas molecules to reach the three-phase limit formed at the electrolyte, based on Knudsen diffusion. As the molecules pass through the pores, the thermo-dynamic equilibrium is established. If the thickness of the catalyzing layer is below 100 to 300 A, then the gas penetration can be effected even without micro pores by what has been termed bulk diffusion.

The catalyzing layer with which the solid electrolyte body is covered on the side exposed to the exhaust gases may be platinum, as above referred to with respect to the drawings; it may, however, also be a platinum alloy with aluminum, cobalt, nickel, chromium, or other platinum metals as components of alloys; or may consist of an oxide system such as copper chrome oxide, optionally doped with barium oxide or nickel oxide, or lanthanum cobalt oxide which may be doped with strontium oxide. The average thickness of the layer is between 0.02 and 20 $\mu$ m (micro meter or $10^{-6}$ meter). The density of the pores must be so selected that at least 0.01 percent of the surface of the catalyzing layer is formed by micro pores or micro fissures.

Catalyst material, and especially the expensive platinum or platinum metals can be saved, if only a portion of the surface of the solid electrolyte is covered by the catalyzing layer — see FIGS. 3–5. The voltage jump is not determined by the quantity of the gas being measured, but rather by the difference in oxygen partial pressure at both sides of the solid electrolyte body. The solid electrolyte body must, however, be covered in that portion where the catalyst is not covering the solid electrolyte body by a gas-tight layer which is resistant to the exhaust gases, in order to prevent direct contact between exhaust gases and the solid electrolyte body, for the reason above discussed. In order to be quite sure that no electrolyte body is exposed, it is desirable to overlap the catalyzing layer, at least partly, by the gas-tight layer, as seen in FIG. 5, at the slanted matching surface between layers 13 and 15. To contact the catalyzing layer, a thin, narrow conductive path is carried to that point from which the voltage is to be taken off by means of a standard conductor or pigtail. The conductive path or strip is preferably covered by the gas-tight, protective layer. This gas-tight protective layer may be of a material which has at least one order of magnitude lower ion conductivity than the solid electrolyte, but it may consist of an electronically conductive material. Potassium aluminum silicate, barium aluminum silicate or barium calcium aluminum silicate, or semiconductive glazes based on silicate or borate glasses with additives of $TiO_2$, MnO or $Fe_3O_4$ can be used.

The solid electrolyte itself may be of cubic stabilized zirconium dioxide, thorium dioxide or mullite. The substances may have fluxes as additives, and particularly desirable is the use of zirconium dioxide containing a flux which, for stabilization of the cubic phase contains calcium oxide and additionally has silicon dioxide added, and possibly also aluminum oxide, in a total quantity of about 1–5% (by weight) preferably 1.5 – 3% (by weight), the aluminum oxide portion, if present at all, being less than or at most equal to the silicon dioxide portion. A particularly suitable composition of the starting material for the flux containing zirconium dioxide is:

85 mol-% monoclinic zirconium dioxide
15 mol-% calcium oxide
1.5 – 3% (by weight) silicon dioxide
1.5 – 3% (by weight) aluminum oxide, the latter two components being related to the sum of the zirconium dioxide and calcium oxide.

Such a composition of the solid electrolyte has the advantage with respect to the customarily used stabilized zirconium dioxide ceramic that the parts can be sintered already at 1600° C rather than at 1800° C to form a dense sintered body. This decreases the production costs thereof. Additionally, comparatively inexpensive raw materials (monoclinic zirconium dioxide, chalk, kaolin, talcum) can be used, which keeps the entire production costs low. An additional advantage is the better workability of the raw material by utilizing the referred to fluxes. It is believed that this is due to the plasticity of kaolin. Additionally, the mechanical strength is increased and a better resistance against temperature shocks is obtained, when compared with the otherwise used zirconium dioxide ceramics.

The additives referred to form, upon sintering, a glass phase with a portion of the calcium oxide and the zirconium dioxide, which permits dense sintering at relatively low temperatures. At an additional magnesium oxide content of the flux, for example by the use of talcum as the silicon dioxide raw material, sintering is somewhat slowed when compared with magnesium-free fluxes. It is still possible to make dense bodies at remarkably lower temperatures by sintering than with flux-free zirconium dioxide base material. Raw materials for fluxes can be, besides the pure oxides, materials which, upon heat treatment change to oxides. Due to costs, silicates are preferred, such as kaolin, wollastonite, talcum, and similar minerals, as well as mixtures thereof. The best results are obtained by the use of kaolin. Zirconium dioxide as raw material need not be stabilized zirconium dioxide, but normally monoclinic zirconium dioxide can be used and mixed together with as much as calcium raw material, such as chalk, as is necessary to stabilize the cubic phase, as well as to form a glass.

The exhaust gases, certainly at operating temperatures, attack other materials and the catalyzing layer, due to its thinness, must be protected against mechanical influences. It is therefore necessary to protect this layer against mechanical and chemical disturbances and damages, in order to obtain measuring elements which have a reasonable and suitable life when in use. This protective layer must be porous to the exhaust gases, so that the exhaust gases can reach the catalyzing layer; additionally, it should be of such composition that the response time of the measuring element is not essentially raised.

In accordance with a feature of the invention, the catalyzing layer is covered with a thin porous protective layer. The covering is in intimate connection; the protective layer is being preferably present in a thickness of from 5 to 500 $\mu$ m. Such a protective layer may use many materials which can stand the operating temperature of the exhaust gases to which the sensing element is exposed, and which can be applied to the catalyzing layer with good adhesion. Metals or metal alloys are suitable, such as copper or nickel chrome alloys; further, oxides, mixtures of various oxides, hard substances such as carbides, borides, nitrides of transistion metals, silicates, such as high temperature or high melting sinterglass, kaolin, talcum, if necessary with the addition of feldspar, nephelite-syenite, or wollastonite, or tubular spar.

The protective layer can be applied in various ways. For example, an aqueous suspension of the material of the protective layer may be applied by brushing, by immersion, by spraying, or applying the substance as a powder or by dusting on the catalyzing layer and thereafter by burning on or sintering the material at temperatures above expected operating temperatures. Higher porosity can be obtained when a material is added which burns off, or is sublimated off upon sintering. A protective layer can also be applied by plasma spray in porous form. A protective layer of chromium oxide can be applied by reactive vaporization, or galvanic chrome plating with subsequent oxidation.

The protective layer is particularly suitable when it, itself, can catalyze the gas to condition of gas equilibrium, since thereby the sharp potential jump is retained even if the catalyzing layer applied directly to the solid electrolyte body is damaged. The protective layer itself then will be made of a ceramic material which is capable of determining the gas equilibrium, and which is catalyzing. Copper chromium oxide has been found to be particularly suitable; this may be doped with barium oxide or nickel oxide. Lanthanum cobalt oxide doped with strontium oxide is also suitable. It is also possible to activate a porous layer which already has been applied to the catalytic layer and which is not, by and itself, catalytically active by impregnating with a solution of one or more noble metals and subsequent thermal decomposition of the noble metal compound to noble metal, for activation.

The catalytically active layer is applied to the solid electrolyte in various ways. For example, the layer can be applied by thin layer techniques, such as thermal vaporization, cathode atomization, gas phase deposition, chemical reduction, galvanic deposition, singly or in combination. To provide a sharp potential jump, which is as pronounced as possible, and to obtain good micro pores or micro fissures, the catalytically active layer, after having been applied to the electrolyte body is then heat-treated, preferably at a temperature of between 200° C and two-thirds of the melting temperature T in ° K of the catalytically active material. The catalytically active layer can, further, be applied to the solid electrolyte by applying a paste of a fine particle ceramic material and a fine particle catalyst material, mixed to a dough with a thinning oil, and applying the paste to the solid electrolyte body. This paste, after application, is then sintered. The catalyzing layer and the solid electrolyte body are then interlocked, increasing the adhesion of the layer. Ceramic material which is suitable preferably is selected to have approximately the same thermal coefficient of expansion as the base solid electrolyte, such as cubic stabilized zirconium dioxide, magnesium spinel or forsterite, possibly with addition of fluxes like feldspar, nepheline, or nepheline-syenite, or Wollastonite. The relationship, by volume, of catalyst to ceramic material, within the paste, should be above about 1 : 5, in order to ensure that the catalyzing material will form a cohesive layer. Interlocking between the catalyzing layer and the base body of the material occurs at the granular limits of the solid electrolyte crystallites.

Specific examples of manufacture: 84.8% (by weight) monoclinic zirconium dioxide 12.1 % (by weight) chalk
3.1 % (by weight) kaolin, as flux are added into a vibration mill, and mixed dry for 4 hours. The mass is shaped thereafter by a combined press and grinding method, well known in the manufacture of spark plug insulators: the mass is compressed with a pressure of 500 kp/cm$^2$, almost isostatically, and the press form is then ground round to the specific shape. Thereafter, the press form is placed into an electrically heated furnace and sintered on a zirconium dioxide substrate. Sintering temperature is about 1600° C with a temperature rise time of about 10 hours and a dwell time at the sintering temperature of about 1 hour. A zirconium dioxide ceramic is obtained which has a bending strength of 2800 kp/cm$^2$. In contrast, commercial stabilized zirconium dioxide ceramics have a bending strength of only about 1,900 kp/cm$^2$. To manufacture large quantities and to provide uniform quantities for each press, it is desirable that the mass is granulated in advance of pressing by use of known binders or press additives, in the manner usual in this technology.

The interior of the tube has an electrode applied thereto in the form of a conductive path, by applying a platinum suspension with a brush.

A conductive path 16 (FIG. 4) is similarly applied at the outside of the solid electrolyte tube 10, the conductive path 16 being carried from the region of the platinum layer 13 — to be applied later — to tne boss or collar 11. Both conductive paths are burned in or sintered at a temperature between 1000° C and 1300° C.

The platinum layer 13 is then vapor-deposited at the lower portion of the tube 10 (FIG. 3). To this end, the tube is secured on an electrically grounded holder and located in a vacuum chamber within a cup-shaped platinum sheet, and rotatably held therefrom by a distance of about 6 cm. The platinum sheet, at the outside, is surrounded by a shielding sheet, at a distance of about 0.5 cm. The vacuum chamber is evacuated to a pressure of less than 10$^{-3}$ Torr. Thereafter, a gas which is non-reactive with platinum, for example argon, is admitted and the pressure is stabilized to between 10$^{-3}$ and 10$^{-1}$ Torr. The holder with the tube is slowly rotated, about 1 rpm, and a pulsating direct current of 4 kV, effective, is placed on the platinum sheet. A glow discharge will occur between the tube and the platinum sheet. The ion current to the platinum sheet, which is connected as cathode, vaporizes the platinum sheet and a platinum deposit will form on the tube. The platinum deposit is kept uniform by rotation of the tube. The cup-shaped platinum sheet is so made that only the portion of the tube which is closed is dusted with platinum. At a current of 2 mA/cm$^2$ at the cathode surface, a deposit time of 15 minutes will result in a layer of about 0.7 $\mu$m. The layer grows by heating during the dusting process initially free from pores. The micro pores, necessary to operate the sensing gauge, are created after dusting, and succeeding the dusting step, by heating to a temperature of 800° C for about 45 minutes. The rise time to this temperature should be as short as possible and is best obtained by inductive heating or by a stream of hot gas.

The catalyst layer 13 can also be applied by thermal vapor deposit at the end of the tube 10 where the layer is to form. To this end, a vacuum vessel is provided in which the tube, rotatable about its longitudinal axis, as well as a vessel with platinum to be vaporized are located in a suitable arrangement. The vessel is evacuated to a pressure less than 10$^{-4}$ Torr, and the platinum is vaporized by an electron beam which is introduced at an angle. Electron beam energies between 30 and 60 kV, and beam currents of from 30 to 60 mA will deposit a layer of 0.7 to 1.0 $\mu$ m on a gauge rotating at about 50 rpm, and provide a platinum layer in a period of time of from 1 to 10 minutes. By suitable adjustment of the pressure of the remaining gas in the vessel and suitable choice of vaporization speed, platinum coatings are obtained which have good adhesion also under cold conditions and have initially sufficient mirco pores or micro fissures to provide for a sharp voltage transition upon sensing of oxygen when in use.

In the next step of the process, the portion of the tube surface which is not covered with platinum is covered with a gas-tight layer in order to prevent direct contact of exhaust gases with the solid electrolyte body. This gas-tight layer is obtained in this manner: A pulverized mixture of quartz, kaolin, feldspar and chalk is made in the following proportions: 72 % SiO$_2$, 16 % Al$_2$O$_3$, 8.5 % K$_2$O and 1.5 % CaO, all percentages by weight. This mixture is stirred with water to a thick suspension and applied to the surface on the tube which is not covered by platinum by means of a brush. With reference to FIG. 5, the layer 15 should slightly overlap platinum layer 13. The solid electrolyte tube with the suspension brushed thereon is heated to a temperature of 1350° C for 8 hours and tempered thereby, the dwell time at the indicated temperature being about an hour.

The porous protective layer is applied as the last step of the process. A layer of aluminum oxide is applied by means of plasma spray technique, in a thickness of about 100 $\mu$ m.

The result of the sequence of steps is a measuring element which shows a sharp voltage jump at transition of the air number from below one to over one, that is, at $\lambda = 1$, so that the sensing element is highly suitable for use in control circuits to control optimum exhaust gas composition. The platinum layer is protected, and the economic life of the measuring or sensing element is much longer than that of previously known elements. The response time is short, and decidedly shorter than in sensing elements in which the platinum layer is not protected.

Various changes can be made in the sensing elements, and in the method of making them. The various materials, as well as the various process steps can be changed, as previously referred to, and equivalent processes and materials may be used.

We claim:

1. Method to make a sensing element for electrochemical sensing of oxygen content in exhaust gases from internal combustion engines, the sensing element being an oxygen concentration cell and including a solid oxygen ion conductive electrolyte body having an inner surface covered at least in part by an inner electrode and an outer surface adapted to contact oxygen from said exhaust gases, the method comprises applying, by means of thin layer techniques, an electron-conductive catalyst layer electrode of a material which catalyzes the gas equilibrium and covering at least part of said outer surface, said material being formed with micro pores in those regions thereof where its thickness is greater than about 100 A, and heating said electron-conductive catalyst layer, after application thereof to the electrolyte body, at a temperature between 200° C and two-thirds the melting temperature T in ° K of said electron-conductive catalyst layer to form said micro pores, and applying an outer protective layer covering all of said electron-conductive catalyst layer and all parts of said outer surface which are not covered by said electron-conductive catalyst layer, at least the part of said outer protective layer covering said electron-conductive layer being porous.

2. Method according to claim 1 wherein said catalyst layer comprises a catalyst selected from the group consisting of platinum, platinum group metals, and alloys of platinum and platinum group metals.

3. Method according to claim 2, wherein the solid electrolyte body comprises a material selected from the group consisting of cubic stablized zirconium dioxide, thorium dioxide, mullite, and each of the foregoing with the addition of a flux selected from the group consisting of kaolin and talc.

4. Method according to claim 2, wherein the solid electrolyte body comprises zirconium oxide and calcium oxide to stablize the cubic phase, and as a flux silicon dioxide and aluminum oxide in a total amount of 1–5% by weight based on the weight of the total of zirconium oxide and calcium oxide, the aluminum oxide being present in amounts of from zero up to equal the amount of silicon dioxide.

5. Method according to claim 3, wherein the stablized zirconium dioxide comprises 85 mol % monoclinic zirconium dioxide and 15 mol % calcium oxide and the flux comprises 1.5 to 3% by weight based on the weight of the total, of the zirconium dioxide and calcium oxide, of silicon dioxide and aluminum oxide, the silicon dioxide and aluminum oxide being in the form of kaolin.

6. Method according to claim 2, wherein the solid electrolyte body comprises a closed tubular element, and said method includes the step of applying said electron-conductive layer over the closed end of the tubular element.

7. Method according to claim 2, wherein the thin layer technique comprises at least one of: thermal vaporization; cathode atomization; deposition from gas phase; chemical reduction; galvanic deposition; or any combination thereof; and wherein said micro pores extend through said catalyst layer.

8. Method to make sensing element for electrochemical sensing of oxygen content in exhaust gases from internal combustion engines, the sensing element being an oxygen concentration cell, comprising
    providing an unsintered raw body of solid oxygen ion conductive electrolyte material;
    applying a paste of fine particle ceramic material and fine particle catalyst material which catalyzes the gas equilibrium with a thinning oil to at least a part of one surface of the solid electrolyte body;
    sintering the body with the paste thereon to form a catalyst layer electrode on said solid electrolyte body, having micro pores extending through said catalyst layer, and applying an outer protective layer covering all of said catalyst layer and all parts of said surface of said solid electrolyte body upon which said catalyst layer is applied and which are not covered by said catalyst layer, at least the part of said outer protective layer covering said electron-conductive layer being porous.

9. Method according to claim 8, wherein said catalyst layer comprises a catalyst selected from the group consisting of platinum, platinum group metals, and alloys of platinum and platinum group metals.

10. Method according to claim 9, wherein the ceramic material comprises a material which has about the same thermal coefficient of expansion as the solid electrolyte body.

11. Method according to claim 10, wherein the ceramic material comprises cubic stabilized zirconium dioxide, magnesium spinel, or fosterite.

12. Method according to claim 11, wherein the ceramic material contains a flux material selected from the group consisting of feldspar, nepheline, nepheline-syenite, and wollastonite.

13. Method according to claim 9, wherein the solid electrolyte body comprises a material selected from the group consisting of cubic stabilized zirconium dioxide, thorium dioxide, mullite, and each of the foregoing with the addition of a flux selected from the group consisting of kaolin and talc.

14. Method according to claim 13, wherein the stabilized zirconium dioxide comprises 85 mol % monoclinic zirconium dioxide and 15 mol % calcium oxide and the flux comprises 1.5 to 3% by weight based on the weight of the total, of the zirconium dioxide and calcium oxide, of silicon dioxide and aluminum oxide, the silicon dioxide and aluminum oxide being in the form of kaolin.

15. Method according to claim 9, wherein the solid electrolyte body comprises zirconium oxide and calcium oxide to stablize the cubic phase, and as a flux silicon dioxide and aluminum oxide in a total amount of 1–5% by weight based on the weight of the total of zirconium oxide and calcium oxide, the aluminum oxide being present in amounts of from zero up to equal the amount of silicon dioxide.

* * * * *